United States Patent [19] [11] 3,979,450
Moskovich et al. [45] Sept. 7, 1976

[54] METHOD FOR PREPARING DICARBOXYLIC ACIDS

[76] Inventors: Jury Leonidovich Moskovich, Moskovsky prospekt, 1, kv. 14; Jury Nikolaevich Juriev, Liteiny prospekt, 46, kv. 17; Viktor Karlovich Tsyskovsky, Kanal Griboedova, 22, kv. 6; Ljudmila Vasilievna Berezova, prospekt Obukhovskoi Oborony, 104, kv. 7; Nokhum Davidovich Gilchenok, ulitsa Ordzhonikidze 11/39, kv. 50, all of Leningrad; Vladimir Avgustovich Yanshevsky, ulitsa Kommunisticheskaya, 7, kv. 28, Novokuibyshevsk; Dmitry Vasilievich Mushenko, Bolzheokhtinsky prospekt, 10, kv. 18, Leningrad; Evgeny Semenovich Zelikman, Novo-Litovskaya ulitsa, 5, kv. 116, Leningrad; Rufina Alexandrovna Filippova, ulitsa, Uspenskogo, 3, kv. 19, Novokuibyshevsk; Vladimir Leonidovich Klimenko, ulitsa, Lomonosova, 12 kv. 29, Leningrad; Valerian Mikhailovich Sobolev, naberezhnaya Maxima Gorkogo, 46-50, kv. 185, Moscow, all of U.S.S.R.

[22] Filed: Feb. 8, 1973

[21] Appl. No.: 330,637

[52] U.S. Cl................. 260/537 P; 260/488 F; 260/491; 260/497 R
[51] Int. Cl.$^2$......................................... C07C 51/26
[58] Field of Search ................ 260/533 D, 537 P

[56] References Cited
UNITED STATES PATENTS

| | | | |
|---|---|---|---|
| 3,014,070 | 12/1961 | Chafetz ........................... | 260/537 P |
| 3,441,604 | 4/1969 | Baylis et al. ..................... | 260/533 D |
| 3,856,833 | 12/1974 | Siclari et al. .................... | 260/537 P |

OTHER PUBLICATIONS

Barley, Chem. Revs. vol. 58 No. 5 (1958).
Kressman, *Manufacturing Chemist*, Nov. 1956.

*Primary Examiner*—Vivian Garner
*Attorney, Agent, or Firm*—Haseltine, Lake & Waters

[57] ABSTRACT

A method for preparing dicarboxylic acids by subjecting cycloolefins to ozonolysis in a medium of lower monocarboxylic acids so as to form an ozonalyzate; treating the ozonalyzate with a solution of hydrogen peroxide; passing the thus obtained mixture through a solid acid catalyst, such as an Amberlite IR-120 cation-exchange resin; and subjecting the thus obtained catalyzed product first to thermal treatment at a temperature of from 50° to 80°C and then to thermal decomposition at a temperature of from 90° to 110°C to form desired dicarboxylic acids such as succinic, suberic or 1,10-decanedicarboxylic acids, depending on the starting cycloolefin, in a yield 98 per cent of the theoretical value and of 99.5 per cent purity.

11 Claims, No Drawings

METHOD FOR PREPARING DICARBOXYLIC ACIDS

This invention relates to the synthesis of petrochemicals, and more particularly relates to a method for preparing dicarboxylic acids by ozonolysis of cycloolefins.

Dicarboxylic acids are used in the synthesis of polyester and polyamide resins and plasticizers.

Already known in the literature are numerous methods for the synthesis of dicarboxylic acids by ozonolysis of cycloolefins such as those disclosed in French Patent No. 1,391,338, British Patents Nos. 971,670 and 965,510 and U.S. Pat. No. 3,219,675.

For example, French patent No. 1,391,338 describes a method for preparing dicarboxylic acids by ozonolysis of cyclododecene in a solution of lower monocarboxylic acids. at a temperature of 25°C with subsequent degradation (by oxidation) of the ozonolyzate in a current of oxygen or air at a temperature gradually increasing from 80° to 110°C. The thermooxidative decomposition of ozonolyzate having the formula

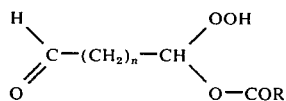

where R is alkyl and $n = 2 - 10$, in a medium of lower monocarboxylic acids at elevated temperature, results in the formation of by-products due to incorporation of oxygen into the aliphatic chain, decarboxylation of the aldehyde group, and formation of solid products. This complicates the process for preparation of the acid of the required quality since complicated and expensive methods for purification are needed. Moreover, the yield of the final product in these methods is not above 70 percent of the theoretical value.

An object of this invention is to increase the yield of dicarboxylic acids that are produced by ozonolysis of cycloolefins.

Another object of the invention is to improve the purity of the obtained dicarboxylic acids.

These and other objects of the invention have been attained by the present method which can be summarized as follows:

Cycloolefins are subjected to ozonolysis at a temperature of from 20° to 40°C (until ozone is detected in the spent gas) in a medium of lower monocarboxylic acids (acetic, propionic, etc.). The resulting ozonolyzate is treated with a 20–30 percent aqueous solution of hydrogen peroxide. Further processing of the thus obtained reaction mixture is carried out in two reaction kettles arranged in series. A solid acid catalyst is contained in the first apparatus, suitable examples of such solid acid catalyst being commercial cation-exchange resins such as those having trade names, e.g., the Soviet Brand name of Ky -2-8 which is an ion-exchange resin having a polystyrene matrix cross-linked with approximately 8% divinylbenzene and containing sulfonic acid groups that have been introduced by sulfonation, which consists of spherical granules ranging from yellow to brown in color, having a moisture content of from 40–60% and having a mechanical strength of from 93–95%, or Amberlite IR-120 of Rohm & Haas, which are ion-exchange resins having a polystyrene matrix cross-linked with approximately 8% of divinylbenzene and containing sulfonic acid groups that have been introduced by sulfonation, or a mineral acid supported on silica gel, for example phosphoric acid, through which the ozonolyzate treated with hydrogen peroxide is passed at a temperature from 30° to 60°C at a volumetric rate of 2–4 $hour^{-1}$. Next, the reaction mixture is passed through the other apparatus at the a temperature of 50°–80°C and at volumetric rate of 0.3–0.5 $hour^{-1}$, whereby the reaction mixture is completely oxidized in the absence of catalysts.

The process of the ozonolyzate oxidation can be represented by the following scheme, with acetic acid and cyclododecene being taken as exemplary substances:

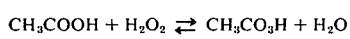

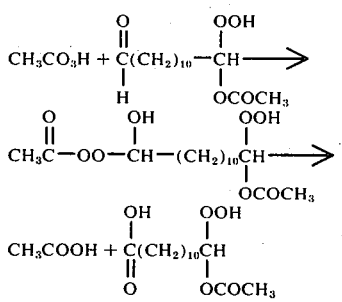

During the first stage, the reaction mixture is contacted with a bed of solid acid catalysts, for example the cation-exchange resin KY-2-8, and, as a result, peracetic acid is formed and a part (about 20–30 percent) of the ozonolyzate is oxidized. In the second step, the ozonolyzate is homogeneously oxidized with the peracetic acid in the absence of catalysts.

The oxidized ozonolyzate discharged from the second apparatus is then delivered to the thermal decomposition stage.

The process is carried out in the absence of catalysts at a temperature of from 90° to 110°C for 2–4 hours. The reaction is as follows:

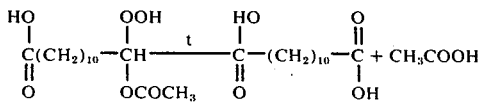

As a result of the said processing, the following products are obtained: - succinic acid (from cyclododecatriene and cyclooctadiene), suberic acid (from cyclooctene), and 1,10-decanedicarboxylic acid (from cyclododecene).

Dicarboxylic acids are isolated from the products of decomposition (which are solutions of the dicarboxylic acid in an aqueous monocarboxylic acid) and purified by a number of different methods whose choice depends on the properties of the particular final acid in question.

The main quantity (about 95–97 percent) of the monocarboxylic acid is distilled together with water at a temperature of from 40° to 50°C and a residual pressure of 50 to 100 mm Hg.

The conditions for rectification are selected depending on the properties of the monocarboxylic acid.

The remaining quantity of the said acid (about 3–5 percent) is distilled at the same residual pressure in the form of an azeotropic mixture, after addition of a suitable solvent (n-heptane, if acetic acid is used as the reaction medium, or ethylbenzene, if propionic acid is used).

The ratio of the monocarboxylic acid to the solvent is 1:6.

After termination of the distillation of the azeotropic mixture the resulting crystals of succinic and suberic acids are dried to remove traces of the solvent at a temperature of from 70° to 80°C for 2 or 3 hours.

In order to isolate 1,10-decanedicarboxylic acid from the aqueous solution of the monocarboxylic acid, the mixture of products emerging from the oxidation kettle is delivered into a heat exchanger operating at a temperature of 100°C, where the oxidized products of cycloolefin ozonolysis are decomposed for three hours, then cooled to 15°–20°C, and the precipitated crystals of 1,10-decanedicarboxylic acid are washed with water from traces of the monocarboxylic acid and dried at a temperature from 70° to 80°C for three hours.

The yield of the dicarboxylic acids is 98–99 percent of theory.

The purity of the acids obtained by the present method and determined by the partition gas chromatographic method is about 99.5 percent.

The preferred conditions for the preparation of the dicarboxylic acids are as follows.

Ozonolysis should preferably be carried out at a temperature of 25°–30°C with ozonized air (ozone content 1.5–2 percent by weight) in a medium of 99.2–99.6 percent acetic acid. Monocarboxylic acids having higher molecular weights should be avoided since they are more expensive and less workable because of the considerable viscosity of the ozonolyzate solutions in these acids.

The oxidation of the ozonolyzate should preferably be carried out with 29–30 percent hydrogen peroxide. The temperature in the reaction kettle, packed with the catalysts through which the reaction mixture is passed, should be about 50°C. The volumetric rate of the oxidized products passage through the catalyst should preferably be 4 hour$^{-1}$. The temperature inside the reaction kettle where the ozonolyzate are finally oxidized should be maintained at about 80°C whereas the volumetric rate of the reaction mixture passage should preferably be 0.5 hour$^{-1}$.

The cation-exchange resin of the Soviet brand name KY-2-8 should preferably be employed as the catalyst.

Mineral acids, for example $H_3PO_4$, $H_2SO_4$ and others, supported on various solid carriers, are less effective compared with the cation exchange resins, which is due to washing out or leaching of the mineral acid which results in a loss of catalyst selectivity.

The thermal decomposition of the oxidized ozonolyzate should preferably be carried out at a temperature of from 100° to 110°C.

For a better understanding of the invention by those skilled in the art, the following non-limiting, representative examples are given hereinbelow.

The advantages of the present method resides in the following:

As a result of the selective reaction of ozone with the double bond, and the subsequent use of the selective reagent hydrogen peroxide, homologs of dicarboxylic acids are not formed and hence their removal from the final product by complicated purification obviated. As a result, the final product does not require special purification;

The use in the process of the acid catalyst which allows the operation to be carried out at great volumetric rates (2-4 hour$^{-1}$) and practically during unlimited periods of time, since it can be easily regenerated with hydrochlororic acid;

Ions of iron which are transferred into the reaction mixture from the apparatus and can decompose the peroxidic ozonolyzate, are quickly exchanged for hydrogen ions and thus do not affect the course of the process.

EXAMPLE 1

16.2 g (0.1 mole) of cyclododecatriene are dissolved in 64.8 g of 99.6 percent acetic acid and ozonized air (containing 2 percent by weight of ozone) is passed through the obtained solution at a temperature of 20°C until ozone appears in the exhaust gas. During the ozonolysis, 4.8 g of acetic acid are carried away with the air current.

38.0 g of 30 percent aqueous solution of hydrogen peroxide are added to the 48.6 g of the ozonolyzate (quantitative conversions) in a solution of 42.0 g of acetic acid, and the obtained mixture is passed at a temperature of 30°C through the cation exchanger packed with resin KY-2-8 at a volumetric rate of 2 hour$^{-1}$. Then the mixture is passed through the other apparatus at a volumetric rate of 0.3 hour$^{-1}$ to ensure complete oxidation of the ozonolyzate without catalysts at a temperature of 50°C.

Then, the oxidized products of ozonolysis, emerging from the second apparatus, are thermally decomposed at a temperature of 110°C for 2 hours. As a result of this treatment, succinic acid is obtained, which is isolated from the decomposition products as follows.

The main quantity (97 percent) of acetic acid is distilled with water at a temperature of 40°C and and a residual pressure of 100 mm Hg. The remaining quantity of acetic acid is distilled at the same pressure and temperature in the form of an azeotropic mixture after addition of n-heptane (the n-heptane to acetic acid ratio is 6:1).

On distillation of the azeotropic mixture, crystals of succinic acid are dried, so as to remove traces of the solvent, at a temperature of 70°C for 2 hours.

35.2 g of succinic acid are produced as a result, which is 99.5 percent of theory or 217 percent by weight with reference to the spent cyclododecatriene.

The properties of the thus-obtained succinic acid are as follows:
melting point, 185°–185.5°C.
acid number, 949 mg of KOH/g
assay (according to chromatographic analysis), 99.9%.

EXAMPLE 2

16.2 (0.1 mole) of cyclododecatriene are dissolved in 64.8 g of 99.6 percent acetic acid and ozonized air containing 2 percent by weight of ozone is passed through the obtained solution at a temperature of 25°C until ozone appears in the exhaust gas. During the process of ozonolysis, 4.8 g of acetic acid are carried away with the air current.

To the 48.6 g of the ozonolyzate in 42.2 g of acetic acid, are added 38.0 g of a 30 percent aqueous solution of hydrogen peroxide, and the obtained mixture is passed at a temperature of 50°C through the reaction kettle packed with cation-exchange resin KY-2-8 at a volumetric rate of 4 hour$^{-1}$.

The mixture is then passed through the other apparatus at a rate of 0.5 hour$^{-1}$ where the ozonolyzate is finally oxidized at a temperature of 80°C. Further processing of the reaction mixture is carried out under conditions similar to those described in Example 1.

As a result, 35.0 g of succinic acid are produced which constitutes 99.4 percent of theory or 217 percent by weight with reference to the spent cyclododecatriene. The succinic acid prepared by the described method has the following characteristics:
melting point, 185°–185.5°C
acid number, 949 mg of KOH/g
assay (according to chromatographic analysis), 99.9%.

EXAMPLE 3

In accordance with the conditions of Example 1, for oxidation of the products of cyclododecatriene ozonolysis, 57.0 g of 20 percent aqueous solution of hydrogen peroxide were taken. After oxidation of the ozonolyzate at a temperature of 50°C in the presence of cation-exchange resin Dowex-50 (whose composition is quite similar to that described for Amberlite IR-20) in the first apparatus, through which it is passed at a volumetric rate of 4 hour$^{-1}$, the ozonolyzate is finally oxidized in the second apparatus at a temperature of 80°C through which it is passed at a rate of 0.5 hour$^{-1}$. The oxidized products are then thermally decomposed at a temperature of 90°C for 4 hours.

Isolation and purification of succinic acid are carried out as described in Example 1.

As a result, 34.8 g of succinic acid are obtained, which constitutes 98.3 percent of the theoretical value or 214 percent by weight with reference to the spent cyclododecatriene.

The characteristics of the final product are as follows:
melting point, 185°–185.5°C.
acid number 949 mg of KOH/g
assay (according to chromatographic data), 99.9%.

EXAMPLE 4

16.2 g of cyclododecatriene (0.1 mole) are dissolved in 56.8 g of 99.5 percent propionic acid. Ozonized oxygen containing 5 percent by weight of ozone is passed through the obtained mixture at a temperature of 25°C until ozone appears in the exhaust gas. As a result, 52.8 g (quantitative conversion) of the product of cyclododecatriene ozonolysis in a solution of 32.6 g of propionic acid are obtained. During the process, 2.0 g of propionic acid are carried away with the oxygen current.

Further processing of the ozonolyzate (first oxidation, final oxidation, and thermal decomposition) are carried out under the conditions described in Example 1.

Isolation of the acid from the products of decomposition (which are a solution of succinic acid in an aqueous solution of propionic acid) is effected as follows.

The main quantity (96 percent) of propionic acid is distilled together with water at a temperature of 50°C and a residual pressure of 50 mm Hg. The remaining quantity of propionic acid is distilled at the same pressure and temperature in the form of an azeotropic mixture after addition of ethylbenzene (the ratio of ethylbenzene to propionic acid being 6:1). After distillation of the azeotropic mixture, crystals of succinic acid are dried to remove traces of ethylbenzene at a temperature of 80°C for 3 hours.

As a result, 34.6 g of succinic acid are produced, which constitutes 97.6 percent of the theoretical value or 212 percent by weight with reference to the spent cyclododecatriene.

The characteristics of the final product are as follows:
melting point, 185–186°C
acid number, 947 mg of KOH/g
assay (according to chromatographic data) 99.6%.

EXAMPLE 5

10.8 g (0.1 mole) of cyclooctadiene are dissolved in 52.0 g of glacial acetic acid and ozonized air containing 1.5 percent of ozone is passed through the obtained solution at a temperature of 30°C until ozone appears in the exhaust gas.

As a result, 32.4 g (quantitative conversion) of the products of cyclooctadiene ozonolysis in a solution of 36.0 g of acetic acid are produced. During the process, 4 g of acetic acid are carried away with the air current.

Then the ozonolyzate is treated with 25.0 g of a 30 percent aqueous solution of hydrogen peroxide. The obtained mixture is passed at a temperature of 30°C and a rate of 2 hour$^{-1}$ through an apparatus packed with cation-exchange resin Amberlite IR-120.

Further processing of the reaction mixture is the same as described in Example 1. As a result, 23.1 g of succinic acid are produced which is 99 percent of the theoretical value or 214 percent with reference to the spent cyclooctadiene.

The characteristics of the final product are as follows:
melting point, 186°–186.5°C
acid number, 948 mg of KOH/g
assay (according to chromatographic data) 99.4%.

EXAMPLE 6

11.0 g (0.1 mole) of cyclooctene are dissolved in 52.0 g of 99.6 percent acetic acid. Ozonized air containing 2.5 percent of ozone is passed through the prepared solution at a temperature of 25°C until ozone appears in the exhaust gas. As a result, 21.4 g (quantitative conversion) of the products of cyclooctene ozonolysis in a solution of 42.0 g of acetic acid are produced. During the process, 4 g of acetic acid are carried away with the air current.

To the obtained solution are added 12.4 g of 30 percent aqueous solution of hydrogen peroxide.

Further processing of the reaction mixture is similar to that described in Example 1.

As a result, 17 g of suberic acid are produced which is 97.7 per cent of the theoretical value or 160 per cent with reference to the spent cyclooctene.

The characteristics of the obtained product are:
melting point, 140°–141°C
acid number, 645 mg of KOH/g
assay (according to chromatographic data) 99.5%.

EXAMPLE 7

16.6 g (0.1 mole) of cyclododecene are dissolved in 66.4 g of 99.6 per cent acetic acid. Ozonized air containing 3 per cent by weight of ozone is passed through the obtained solution at a temperature of 20°C. As a result, 27.2 g (quantitative conversion) of the products of cyclododecene ozonolysis in a solution of 54.4 g of acetic acid are produced. During the process, 6 g of acetic acid are carried away with the air current.

To the solution of the product of cyclododecene ozonolysis are added 12.7 g of 30 per cent solution of hydrogen peroxide, after which the reaction mixture is passed through the action exchanger packed with resin KY-2-8 at a rate of 2 hour$^{-1}$ at a temperature of 30°C.

Further, the mixture is passed through the second apparatus at a volumetric rate of 0.3 hour$^{-1}$ where the products of ozonlysis are finally oxidized at a temperature of 50°C without catalysts. The mixture is then delivered into a heat exchanger operating at a temperature of 100°C where the oxidized ozonolyzate is decomposed for 3 hours, after which the solution is cooled to 20°C, the precipitated crystals of 1,10-decanedicarboxylic acid are separated on a filter, washed with water of traces of acetic acid and dried at a temperature of 80°C for 3 hours.

As a result, 22.8 g of 1,10-decanedicarboxylic acid are produced which is 99.1 percent of the theoretical value, or 137 percent by weight with reference to the spent cyclododecene. 137

The specifications of the product are as follows:
melting point, 128°C
acid number, 486 mg of KOH/g
assay (according to chromatographic data) 99.5%.

EXAMPLE 8

16.6 g (0.1 mole) of cyclododecene are dissolved in 66.4 g of 9.5 percent propionic acid. Ozonized air containing 3 percent by weight of ozone is passed through the prepared solution at a temperature of 40°C until ozone is detected in the exhaust gas.

As a result, 28.6 g (quantitative conversion) of the product of cyclododecene ozonolysis in a solution of 54.6 g of propionic acid are obtained. During the process, 5 g of propionic acid are carried away with the air current.

Further processing of the ozonolyzate is carried out under conditions similar to those described in Example 7.

As a result, 22.3 g of 1,10-decanedicarboxylic acid are produced which is 98 percent of the theoretical value or 134 percent by weight with reference to the spent cyclododecene.

The specifications of the product are as this:
melting point, 127.6°C
acid number, 487 mg of KOH/g
assay (according to chromatographic data) 99.9%.

EXAMPLE 9

The quantity of the starting cyclododecene, the conditions for its ozonolysis and further processing of the ozonolyzate are the same as described in Example 7, except that the ozonolyzate is oxidized with 20 g of 20 percent solution of hydrogen peroxide.

As a result, 22.5 g of 1,10-decanedicarboxylic acid are produced, which is 98.4 percent of the theoretical value, or 134.5 percent with reference to the spent cyclododecene.

The specifications of the final product are as follows:
melting point, 128.2°C
acid number, 486 mg of KOH/g
assay (according to chromatographic data), 98.9%.

EXAMPLE 10

The quantity of the starting cyclododecene, conditions for its ozonolysis and further processing are similar to those described in Example 7, except that the ozonolyzate is passed through the column packed with a solid acid catalyst Dowex-50 at a rate of 4 hour$^{-1}$ at a temperature of 60°C, and is then passed through the other apparatus at a rate of 0.5 hour$^{-1}$ where the ozonolyzate finally oxidized at a temperature of 80°C in the absence of catalysts.

As a result, 22.2 g of 1,10-decanedicarboxylic acid are produced which make 97.5 percent of theory of 133.1 percent by weight with reference to the spent cyclododecene.

The characteristics of the final product are as follows:
melting point, 128°C
acid number, 488 mg of KOH/g
assay (according to chromatographic data) 98.0%.

While a specific embodiment of the invention has been disclosed in the description, it will be understood that various modifications within the spirit of the invention may occur to those skilled in the art without departing from the function and scope of the invention as hereinafter defined by the appended claims.

We claim:

1. A method for preparing dicarboxylic acids, comprising ozonolyzing a cycloolefin reactant with ozonized air in a lower alkanoic acid medium at a temperature of from 20° to 40°C to form an ozonolyzate; treating the ozonolyzate with an aqueous solution of hydrogen peroxide having a concentration of from 20 to 30 percent of said hydrogen peroxide; passing the obtained mixture through a solid acid catalyst which is a cation exchange resin having a polystyrene matrix cross-linked with divinylbenzene and containing sulfonic acid groups, said cation exchange resin being in the H-form at a temperature of from 30° to 60°C at a space velocity of from 2 to 4 hours$^{-1}$; heat-treating the cartalyzed product to a temperature of from 50° to 80°C and at a space velocity of from 0.3 to 0.5 hour$^{-1}$; and thermally degrading the heat-treated catalyzed product at a temperature of from 90° to 110°C.

2. A method as claimed in claim 1, wherein the cycloolefin reactant is cyclododecatriene.

3. A method as claimed in claim 1, wherein the cycloolefin rectant is cyclododecene.

4. A method as claimed in claim 1, wherein the cycloolefin reactant is cyclooctadiene.

5. A method as claimed in claim 1, wherein the cycloolefin reactant is cyclooctene.

6. A method as claimed in claim 1, wherein the ozonolyzate is treated with a 29–30 percent aqueous solution of hydrogen peroxide.

7. A method as claimed in claim 1, wherein said lower alkanoic acid is 99.2–99.6 percent acetic acid.

8. A method as claimed in claim 1, wherein the ozonolyzate is passed through a solid acid catalyst at a volumetric rate of 4 hour$^{-1}$ at a temperature of 50°C.

9. A method as claimed in claim 1, wherein the catalyzed product is thermally treated at a rate of 0.5 hour$^{-1}$ at a temperature of 80°C.

10. A method as claimed in claim 1, wherein said catalyst is a cation-exchange resin having a polystyrene matrix cross-linked with approximately 8% of divinylbenzene and containing sulfonic acid groups.

11. A method for preparing dicarboxylic acids, comprising ozonolyzing a cycloolefin reactant with ozonized air in a lower alkanoic acid medium at a temperature of from 20° to 40°C to form an ozonolyzate; treating the ozonolyzate with an aqueous solution of hydrogen peroxide having a concentration of from 20 to 30 percent of said hydrogen peroxide; passing the obtained mixture through a solid acid catalyst consisting of phosphoric acid supported on a silica gel at a temperature of from 30° to 60°C at a space velocity of from 2 to 4 hours$^{-1}$; heat-treating the catalyzed product to a temperature of from 50° to 80°C and at a space velocity of from 0.3 to 0.5 hour$^{-1}$; and thermally degrading the heat-treated catalyzed product at a temperature of from 90°C to 110°C.

* * * * *